(12) United States Patent
Albenge et al.

(10) Patent No.: US 11,802,214 B2
(45) Date of Patent: Oct. 31, 2023

(54) PROCESS OF PREPARATION OF AN AQUEOUS GEL INK WITH VARIABLE COLOR COMPRISING SILVER NANOPARTICLES

(71) Applicants: SOCIETE BIC, Clichy (FR); UNIVERSITE DE HAUTE ALSACE, Mulhouse (FR); CENTRE NATIONAL DE LA RECHERCHE SCIENTIFIQUE, Paris (FR)

(72) Inventors: Olivier Albenge, Clichy (FR); Romain Metillon, Clichy (FR); Karine Mougin, Paris (FR); Feriel Ghellal, Clichy (FR); Arnaud Spangenberg, Mulhouse (FR)

(73) Assignees: SOCIETE BIC, Clichy (FR); UNIVERSITE DE HAUTE ALSACE, Mulhouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 122 days.

(21) Appl. No.: 17/631,115

(22) PCT Filed: Aug. 28, 2020

(86) PCT No.: PCT/EP2020/074117
§ 371 (c)(1),
(2) Date: Jan. 28, 2022

(87) PCT Pub. No.: WO2021/038064
PCT Pub. Date: Mar. 4, 2021

(65) Prior Publication Data
US 2022/0275228 A1    Sep. 1, 2022

(30) Foreign Application Priority Data
Aug. 29, 2019    (EP) .................................... 19306053

(51) Int. Cl.
C09D 11/17    (2014.01)
C07C 69/618    (2006.01)
B43K 1/12    (2006.01)
B82Y 30/00    (2011.01)

(52) U.S. Cl.
CPC ............. C09D 11/17 (2013.01); B43K 1/12 (2013.01); B82Y 30/00 (2013.01); C07C 69/618 (2013.01)

(58) Field of Classification Search
CPC ....... C09D 11/17; C09D 11/16; C07C 69/618; B43K 1/12; B43K 1/006; B82Y 30/00

USPC ................... 401/198; 523/215; 524/492, 493
See application file for complete search history.

(56) References Cited

U.S. PATENT DOCUMENTS

| | | | |
|---|---|---|---|
| 5,630,868 A | 5/1997 | Belmont et al. | |
| 7,291,292 B2 * | 11/2007 | Ittel ...................... | C09D 11/322 252/500 |
| 8,870,998 B2 * | 10/2014 | Nolte ..................... | B82Y 30/00 75/371 |
| 9,975,110 B1 | 5/2018 | Chou et al. | |
| 2011/0251293 A1 | 10/2011 | Trummer et al. | |

FOREIGN PATENT DOCUMENTS

| | | |
|---|---|---|
| CN | 1994632 A | 7/2007 |
| CN | 105504984 A | 4/2016 |
| CN | 106867315 A | 6/2017 |
| CN | 107022241 A | 8/2017 |
| CN | 107750267 A | 3/2018 |
| CN | 108776127 A | 11/2018 |
| CN | 110016257 A | 7/2019 |
| EP | 3450513 A1 | 3/2019 |
| JP | 2008297323 A | 12/2008 |
| KR | 20080006684 A | 1/2008 |
| WO | 2006072959 A1 | 7/2006 |
| WO | 2019122017 A1 | 6/2019 |

OTHER PUBLICATIONS

International Search Report and Written Opinion in International Application No. PCT/EP2020/074117, dated Nov. 6, 2020 (12 pages).
Teyssier, J. et al., "Photonic crystals cause active colour change in chameleons," Nature Communications, vol. 6, pp. 1-7 (2015).

* cited by examiner

Primary Examiner — David J Walczak
(74) Attorney, Agent, or Firm — Bookoff McAndrews, PLLC

(57) ABSTRACT

A process for preparing in situ an aqueous gel ink with variable color comprising the following steps: (i) preparing a gel-based matrix of aqueous ink comprising an N-Acyl-aminophenol, wherein the hydroxyl group is preferably in meta or para position on the benzenic group, and (ii) adding a solution of silver salts to the gel-based matrix of aqueous ink prepared in step (i), to obtain an aqueous gel ink with variable color with silver nanoparticles disposed therein. An aqueous gel ink with variable color obtained according to process for preparing, comprising an N-Acyl-aminophenol, wherein the hydroxyl group is preferably in meta or para position on the benzenic group and silver nanoparticles. A writing instrument comprising an aqueous gel ink with variable color.

20 Claims, No Drawings

PROCESS OF PREPARATION OF AN AQUEOUS GEL INK WITH VARIABLE COLOR COMPRISING SILVER NANOPARTICLES

CROSS-REFERENCE TO RELATED APPLICATIONS

This application is the U.S. national phase entry under 35 U.S.C. § 371 of International Application No. PCT/EP2020/074117, filed Aug. 28, 2020, which claims priority to European Patent Application No. 19306053.0, filed Aug. 29, 2019, the entire contents of which are incorporated herein by reference.

The present invention concerns a process for preparing in situ an aqueous gel ink with variable color, and to aqueous gel inks with variable color comprising an N-Acyl-aminophenol, wherein said hydroxyl group is preferably in meta or in para position on the benzenic group, preferably in para position, preferably an N-Acyl-aminophenol of formula HO—R1-NH—CO—R2 wherein R1 is a benzene ring and R2 is an alkyl group comprising preferably from 1 to 6 carbon atoms, preferably from 1 to 3 carbon atoms, preferably the hydroxyl group is preferably in meta or in para position, preferably in para position and silver nanoparticles, obtained according to the process of the invention, and free from any dye and pigment. The invention also concerns a writing instrument comprising an aqueous gel ink with variable color according to the invention.

In nature, changing colors are frequently observed in the animal's world, either for camouflage or for courting by respectively fading in or standing out from the environment. Numerous living organisms can rapidly alter their appearance in response to changes in the environment. The most well-known examples are chameleons that are able to quickly change the color of their skin by aggregating or dispersing pigments within dermal chromatophores (J. Teyssier et al., Nature Communications 6, 2014, 6368).

Currently, there are two types of change in color present in nature that researches focus on structural and plasmonic color.

The structural color is observable on the wings of the morpho butterflies or on some plants and fruits. The color change is due to the light reflecting on the microstructures. Their specific shape ensures that the angle by which the light hits the wing influences the color reflected.

The plasmonic color effect is deeper than for the structural color. In fact, the change in color is due to both the light absorption by silver nanoparticles and the spacing between them in the material. This effect can, for example, be observed amongst the chameleons. Indeed, the color of their skin can change if they get excited. The change of color is due to the guanine crystals contained in their skin, which get farther away from each other when they get angry.

Replicating the way animals change their color is not exactly practical for some types of objects, though it can be the inspiration for another approach of creating a color change in other matrix. On this basis, the inventors have surprisingly found that it is possible to obtain new aqueous gel inks that are capable of changing color when writing by replacing former aqueous gel inks containing dyes and pigments by new ones that are nanoparticles-based. Therefore, one of the main objectives of the present invention is to replace all types of dyes and pigments normally present in aqueous gel inks, which have the disadvantage of being expensive and causing high production costs. Another objective of the present invention is to replace all types of dyes and pigments normally present in aqueous gel inks, which have the disadvantage of being irritating to biological membranes, for example skin and eyes, and may cause allergies. Furthermore, the inventors have surprisingly found that the new aqueous gel inks containing nanoparticle-based are also resistant to UV light thereby improving light stability over time.

To this end, the inventors have developed a specific process through which it is possible to obtain new aqueous gel inks with variable color when writing by replacing former aqueous gel inks containing dyes and pigments by new ones that are nanoparticles-based. The process developed within the framework of the invention also presents the advantage of being performed in aqueous media, and therefore to be a "green process". In addition, the process of the invention is performed at low temperature ranges, works in an ecologically viable manner, and also takes account of ecological requirements.

The present invention relates to a process for preparing in situ an aqueous gel ink with variable color comprising the following steps:
 (i) preparing a gel-based matrix of aqueous ink comprising an N-Acyl-aminophenol, wherein said hydroxyl group is preferably in meta or in para position on the benzenic group, preferably in para position, preferably an N-Acyl-aminophenol of formula HO—R1-NH—CO—R2 wherein R1 is a benzene ring and R2 is an alkyl group comprising preferably from 1 to 6 carbon atoms, preferably from 1 to 3 carbon atoms, preferably the hydroxyl group is preferably in meta or in para position, preferably in para position,
 (ii) adding a solution of silver salts to the gel-based matrix of aqueous ink prepared in step (i), to obtain an aqueous gel ink with variable color with silver nanoparticles dispersed therein.

In the sense of the invention, the term "in situ" means that the silver nanoparticles present in the aqueous gel ink of the invention are synthetized directly in the gel-based matrix of the aqueous ink.

In the sense of the invention, the term "variable color" is intended to mean that the color of the aqueous gel ink by visual observation is not the same before application on absorbing support, and after application on absorbing support, specifically paper, cardboard or textiles.

In fact, the change of color is preferably immediately observed (in particular in less than 5 seconds, preferably less than one second) by visual observation when the aqueous gel ink according to the invention is deposited on absorbing support.

For the purposes of the present invention, the term "ink" is intended to mean a "writing ink" which is intended to be used in a writing instrument, and in particular in a pen. A writing ink should not be confused with a "printing ink" which is used in printing machines and which does not have the same technical constraints and thus the same specifications. Indeed, a writing ink must not contain solid particles of which the size is greater than the channels of the writing instrument, in order to avoid blocking them, which would inevitably lead to writing being irreversibly stopped. In addition, it must allow an ink flow rate suitable for the writing instrument used, in particular a flow rate of between 100 and 500 mg/200 m of writing, and advantageously between 150 and 400 mg/200 m of writing. It must also dry sufficiently rapidly to avoid smudging the writing medium. It must also avoid the problems of migration (bleeding) over time. Thus, the ink according to the present invention will be suitable for the writing instrument for which it is intended, in particular for a pen.

In addition, a "writing ink" must not be too fluid, so as to avoid leaks during writing. However, it must be sufficiently fluid to facilitate the flow of the writing action.

In the particular case of the invention, the writing ink can be more specifically a "gel ink" (which corresponds therefore to a thixotropic ink), in particular the viscosity measured at rest (at a shear rate of $0.01\ s^{-1}$) at 20° C. is different and in particular higher than the viscosity measured with a shear rate of $100\ s^{-1}$ at 20° C. using the same rheometer such as a cone-and-plate rheometer for example Malvern KINEXUS with a cone of 60 mm and an angle of 1°. In a particular embodiment, the viscosity of the gel ink according to the present invention measured under these conditions ranges from 1,000 to 7,000 mPa·s, advantageously from 2,000 to 5,000 mPa·s, and more advantageously from 2,500 to 3,500 mPa·s, with a shear rate of $1\ s^{-1}$, and advantageously from 5 to 50 mPa·s, more advantageously from 7 to 40 mPa·s, and still more advantageously from 10 to 20 mPa·s with a shear rate of $5,000\ s^{-1}$. Advantageously, such a viscosity is stable during storage for at least three months at 40° C. and 20% relative humidity, in particular the viscosity will not have a more than 50% decrease. More advantageously, the return to viscosity at rest after shear is very quick, advantageously at most a few minutes, in order to avoid the static leakage in the minutes after writing.

In the present invention, the gel-based matrix of aqueous ink prepared in step (i) may comprise from 50 to 95%, preferably from 60 to 90%, and more preferably from 70 to 85%, by weight of water.

The gel-based matrix of aqueous ink prepared in step (i) may also comprise classic gel ink ingredients such as solvents, antimicrobial agents, corrosion inhibitors, antifoam agents, rheology modifiers, etc. The gel ink ingredients used to prepare the gel-based matrix of aqueous ink of step (i) will be largely described below, in relation with the subject-matter of the aqueous gel ink with variable color of the invention.

According to a preferred embodiment of the invention, the process for preparing in situ an aqueous gel ink with variable color comprising the following steps:
(i) preparing a gel-based matrix of aqueous ink comprising an N-Acyl-aminophenol, wherein said hydroxyl group is in para position on the benzenic group,
(ii) adding a solution of silver salts to the gel-based matrix of aqueous ink prepared in step (i), to obtain an aqueous gel ink with variable color with silver nanoparticles dispersed therein.

According to a preferred embodiment of the invention, the process for preparing in situ an aqueous gel ink with variable color comprising the following steps:
(i) preparing a gel-based matrix of aqueous ink comprising an N-Acyl-aminophenol of formula HO—R1-NH—CO—R2 wherein R1 is a benzene ring and R2 is an alkyl group comprising from 1 to 6 carbon atoms and the hydroxyl group is in para position,
(ii) adding a solution of silver salts to the gel-based matrix of aqueous ink prepared in step (i), to obtain an aqueous gel ink with variable color with silver nanoparticles dispersed therein.

According to a preferred embodiment of the invention, the process for preparing in situ an aqueous gel ink with variable color comprising the following steps:
(i) preparing a gel-based matrix of aqueous ink comprising an N-Acyl-aminophenol of formula HO—R1-NH—CO—R2 wherein R1 is a benzenic ring and R2 is an alkyl group comprising from 1 to 3 carbon atoms and the hydroxyl group is in para position,
(ii) adding a solution of silver salts to the gel-based matrix of aqueous ink prepared in step (i), to obtain an aqueous gel ink with variable color with silver nanoparticles dispersed therein.

In the most preferred embodiment of the invention, said N-Acyl-aminophenol is N-acetyl-para-aminophenol. According to this preferred embodiment, in formula HO—R1-NH—CO—R2, R1 is a benzene ring, R2 is a methyl radical, and the hydroxyl group is in para position.

The N-acetyl-para-aminophenol (CAS number: 103-90-2), also known as paracetamol or acetaminophen, may be purchased under different trade name such as Doliprane, Tylenol, Calpol, Panadol, Dafalgan, Efferalgan, etc. N-acetyl-para-aminophenol is normally used to treat pain and fever, but its use has never been mentioned in the field of inks. The N-acetyl-para-aminophenol may be added in the form of a solution or in the form of powder in the process of the invention.

In particular the N-Acyl-aminophenol according to the invention reduces the silver salts to elemental silver (i.e. oxidation state: 0).

In a preferred embodiment, the concentration of N-Acyl-aminophenol according to the invention in the gel-based matrix of aqueous ink of step (i) ranges from 0.10 to 0.30 mol·$L^{-1}$, and preferably from 0.15 to 0.25 mol·$L^{-1}$.

In the present invention, the solution of silver salts ($Ag^+$) is advantageously a solution of nitrate silver $AgNO_3$. Silver nanoparticles are formed when contacting the silver salts with the N-Acyl-aminophenol according to the invention.

In a preferred embodiment, the concentration of silver salts in the gel-based matrix of aqueous ink of step (ii) ranges from 0.03 to 0.06 mol·$L^{-1}$, and preferably 0.035 to 0.045 mol·$L^{-1}$.

The addition of a solution of silver salts to the gel-based matrix of aqueous ink prepared in step (i) can be made by continuous injection.

In a preferred embodiment, the silver nanoparticles have the shape of spheres or polyhedral shape, preferably polyhedral shape, and more preferably triangular, square, rectangular shapes.

In a preferred embodiment, the molar ratio between the silver salts and the N-Acyl-aminophenol according to the invention ranges from 0.18:1 to 0.30:1, and preferably from 0.20:1 to 0.24:1.

The present invention also concerns an aqueous gel ink with variable color obtained according to the process of the invention, said aqueous gel comprising the N-Acyl-aminophenol according to the invention.

The process according to the invention enables to obtain an aqueous ink composition which exhibits a plasmon effect (plasmon color).

According to a preferred embodiment, the present invention concerns an aqueous gel ink with variable color, said aqueous gel comprising ink comprising said N-Acyl-aminophenol of formula HO—R1-NH—CO—R2 wherein R1 is a benzene ring and R2 is an alkyl group comprising preferably from 1 to 6 carbon atoms, preferably from 1 to 3 carbon atoms, preferably the hydroxyl group is preferably in meta or in para position, preferably in para position and silver nanoparticles.

According to a preferred embodiment, the present invention concerns an aqueous gel ink with variable color, said aqueous gel ink comprising N-acetyl-para-aminophenol and silver nanoparticles.

The N-Acyl-aminophenol, and silver nanoparticles of the aqueous gel ink of the invention are as defined above in relation with the subject-matter of the process of the invention.

Depending on their size, shape, and distance, the color of the dispersion of the silver nanoparticles can change, as well as its properties. This is due to the plasmon resonance. The exposure of the silver nanoparticles to a certain frequency of waves brings the electrons to gather in a certain place, which changes in accordance with the size and shape of the silver nanoparticles. This agglomeration of electrons provokes an anisotropy of the silver nanoparticles, which will then lead to a change of light absorption and scattering, resulting in a specific color. Plasmon resonance is also affected by the distance between the silver nanoparticles due to the coupling of said silver nanoparticles. Indeed, the closer the silver nanoparticles are, the more they will interact with each other, which will increase their coupling effect also called plasmon effect. In the same way, the shape influences the plasmon resonance.

In the aqueous gel ink with variable color of the invention, the amount of the N-Acyl-aminophenol according to the invention advantageously ranges from 2 to 5%, and more advantageously from 3 to 4%, by weight relative to the total weight of the aqueous gel ink.

In the aqueous gel ink with variable color of the invention, the silver nanoparticles have preferably the shape of spheres or polyhedral shape, preferably polyhedral shape, and more preferably triangular, square, rectangular shapes.

In the aqueous gel ink with variable color of the invention, the silver nanoparticles of the invention have preferably an average particle size ranging from 20 to 200 nm, and more preferably from 75 to 150 nm. This average particle size is determined by analysis of 2D images (microscope: JEOL ARM 200), according to the standard ISO9001:2015.

In the aqueous gel ink with variable color of the invention, the amount of silver nanoparticles advantageously ranges from 0.5 to 0.8%, and more advantageously from 0.6 to 0.7%, by weight relative to the total weight of the aqueous gel ink.

In the aqueous gel ink with variable color of the invention, the amount of water advantageously ranges from 50 to 95%, more advantageously from 60 to 90%, and even more advantageously from 70 to 85%, by weight relative to the total weight of the aqueous gel ink.

The aqueous gel ink with variable color of the invention may also comprise classic gel ink ingredients such as solvents, antimicrobial agents, corrosion inhibitors, antifoam agents, rheology modifiers, as described below. These gel ink ingredients are added to the gel-based matrix of aqueous ink in step (i) of the process of the invention.

The aqueous gel ink of the invention may comprise a solvent. Among the solvents that can be used, mention may be made of polar solvents miscible in water such as:
- glycol ethers such as triethylene glycol, polyethylene glycol, diethylene glycol monoethyl ether, diethyleneglycol-mono butyl ether, dipropyleneglycol monobutyl ether, tripropylene glycol monomethyl ether, phenoxyethanol, phenoxypropanol,
- alcohols: linear or branched alcohol in $C_1$-$C_{15}$ such as isopropanol, butanol, isobutanol, pentanol, benzyl alcohol, glycerin, diglycerin, polyglycerin,
- esters such as ethyl acetate or propyl acetate,
- carbonate esters such as propylene carbonate or ethylene carbonate,
- ketones such as methylisobutylketone (MIBK), acetone or cyclohexanone, and mixtures thereof.

In a preferred embodiment, the solvent is chosen in the group consisting of glycol ethers, and more preferably is chosen in the group consisting of triethylene glycol, polyethylene glycol, diethylene glycol monoethyl ether, diethylene-glycol-mono butyl ether, dipropyleneglycol monobutyl ether, tripropylene glycol monomethyl ether, phenoxyethanol, phenoxypropanol, and mixtures thereof. In a further advantageous embodiment the solvent is chosen in the group consisting of triethylene glycol, polyethylene glycol, and mixture thereof.

Advantageously, the solvent is present in the aqueous gel ink of the invention in an amount ranging from 5 to 35%, more advantageously from 9 to 30%, and even more advantageously from 11 to 25%, by weight relative to the total weight of the aqueous gel ink.

The aqueous gel ink of the invention may comprise an antimicrobial agent such as isothiazolinone (ACTICIDE® from Thor), preferably chosen in the group consisting of 1,2-benzisothiazolin-3-one, 2-methyl-4-isothiazolin-3-one, and mixture thereof.

Advantageously, the antimicrobial agent is present in the aqueous gel ink of the invention in an amount ranging from 0.01 to 0.5%, and more advantageously from 0.1 to 0.2%, by weight relative to the total weight of the aqueous gel ink.

The aqueous gel ink of the invention may comprise a corrosion inhibitor, preferably chosen in the group consisting of tolytriazole, benzotriazole, and mixture thereof.

Advantageously, the corrosion inhibitor is present in the aqueous gel ink of the invention in an amount ranging from 0.05 to 1%, more advantageously from 0.07 to 0.5%, and even more preferably from 0.08 to 0.15%, by weight relative to the total weight of the aqueous gel ink.

The aqueous gel ink of the invention may comprise an antifoam agent, preferably a polysiloxane-based antifoam agent, and more preferably an aqueous emulsion of modified polysiloxane (such as MOUSSEX® from Synthron, TEGO® Foamex from Evonik).

Advantageously, the antifoam agent is present in the aqueous gel ink of the invention in an amount ranging from 0.05 to 1%, more advantageously from 0.1 to 0.5%, and even more advantageously from 0.2 to 0.4%, by weight relative to the total weight of the aqueous gel ink.

The aqueous gel ink of the invention may comprise a rheology modifier capable of generating a gelling effect, preferably chosen in the group consisting of xanthan gum, gum arabic, and mixture thereof.

Advantageously, the rheology modifier is present in an amount ranging from 0.08 to 2%, more preferably from 0.2 to 0.8%, and even more preferably from 0.3 to 0.6%, by weight relative to the total weight of the aqueous gel ink.

The aqueous gel ink with variable color of the invention may also comprise other additives such as:
- pH regulators like sodium hydroxide and triethanolamine,
- lubricants,
- coalescing agents,
- crosslinking agents,
- wetting agents,
- plasticizers,
- antioxidants, and
- UV stabilizers.

When present, these additives are added to the gel-based matrix of aqueous ink in step (i) of the process of the invention.

In one aspect, the invention relates to a process for preparing in situ an aqueous ink, with variable color comprising the following steps:

(i) preparing a matrix of aqueous ink, comprising an N-Acyl-aminophenol, wherein said hydroxyl group is preferably in meta or in para position on the benzenic group, preferably in para position, preferably an N-Acyl-aminophenol of formula HO—R1-NH—CO—R2 wherein R1 is a benzene ring and R2 is an alkyl group comprising preferably from 1 to 6 carbon atoms, preferably from 1 to 3 carbon atoms, preferably the hydroxyl group is preferably in meta or in para position, preferably in para position, (ii) adding a solution of silver salts to the matrix of aqueous ink, prepared in step (i), to obtain an aqueous ink, with variable color with silver nanoparticles dispersed therein.

In one aspect, the invention relates to an aqueous ink with variable color obtained according to the above-mentioned process, in particular comprising the N-Acyl-aminophenol, in particular which is as defined in the present disclosure.

The aqueous ink with variable color of the invention may also comprise classic ink ingredients as described previously such as solvents, antimicrobial agents, corrosion inhibitors, antifoam agents, rheology modifiers. These ingredients are added to the matrix of aqueous ink in step (i) of the process of the invention.

In one aspect, the invention relates to the use of the aqueous ink, more specifically of the aqueous gel ink, of variable color as defined above for writing onto an absorbing support. In one embodiment, the absorbing support is a porous substrate, specifically paper, cardboard, or textiles.

The present invention also concerns a method of writing with an aqueous ink, more specifically an aqueous gel ink, of variable color comprising the step of writing onto an absorbing support, wherein the absorbing support is a porous substrate, specifically paper, cardboard or textiles, with an aqueous ink with variable color according to the invention.

After writing onto an absorbing support with the aqueous gel ink of variable color of the invention, the distance between the silver nanoparticles within the aqueous gel ink applied on absorbing support is lower than 500 nm, preferably varies from 10 nm to 100 nm, and more preferably varies from 10 to 50 nm.

Finally, the present invention concerns a writing instrument comprising:
- an axial barrel containing the aqueous ink, more specifically the aqueous gel ink according to the invention, and
- a pen body which delivers the aqueous ink stored in the axial barrel.

The writing instrument of the invention may be chosen in the group consisting of gel pens, felt pens, correction fluid, markers, and preferably gel pens.

In addition to the foregoing, the invention also comprises other provisions which will emerge from the additional description which follows, which relates to the preparation of aqueous gel inks with variable color according to the process of the invention.

EXAMPLES

Example 1: Preparation of an Aqueous Gel Ink with Variable Color Based on N-acetyl-para-aminophenol and Silver Nanoparticles, According to the Process of the Present Invention In a first step (i), a gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additie® RC8221 (corrosion inhibitor). The mixture was homogenised with a homogenizer mixer at a speed of 15 m·s$^{-1}$ during 15 minutes and heated at a temperature of 35° C. Then, 0.40 g of xanthan gum (rheology modifier) was added to the mixture. The mixture was homogenized with a homogenizing mixer at a speed of 15 m·s$^{-1}$ during 15 minutes at a temperature of 35° C. 80.01 g of deionized water was slowly added to the mixture. The mixture was left to stand for 2 h30. Then, 0.30 g of Moussee® S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 0.047 g of N-acetyl-para-aminophenol (Doliprane 1000 mg from Sanofi). The mixture was homogenised with a homogenizer mixer at a speed of 400 rpm during 5 minutes.

In a second step (ii), 300 μL of a solution of silver nitrate (Carl Roth) (200 mM) was introduced into the mixture at a speed of 400 rpm during 10 minutes.

After the addition of the solution of silver nitrate by continuous injection, the color of the aqueous gel ink changed from transparent to grey.

The average particle size of the silver nanoparticles present within the aqueous gel ink is of 100 nm by analysis of 2D images (microscope: JEOL ARM 200), according to the standard ISO9001:2015.

When the obtained aqueous gel ink with variable color was written on cellulosic paper, the color changed from grey to dark brown immediately (<1 second) through a dissemination process of the silver nanoparticles on cellulosic paper.

Thus, the color of the ink is not the same before application on cellulosic paper and after application on cellulosic paper.

Comparative Example 1: Preparation of an Aqueous Gel Ink with N-acetyl-para-aminophenol and Gold Nanoparticles In a first step (i), a gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additie® RC8221 (corrosion inhibitor). The mixture was homogenised with a homogenizer mixer at a speed of 15 m·s$^{-1}$ during 15 minutes and heated at a temperature of 35° C. Then, 0.40 g of xanthan gum (rheology modifier) was added to the mixture. The mixture was homogenized with a homogenizing mixer at a speed of 15 m·s$^{-1}$ during 15 minutes at a temperature of 35° C. 80.01 g of deionized water was slowly added to the mixture. The mixture was left to stand for 2 h30. Then, 0.30 g of Moussee® S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 0.047 g of N-acetyl-para-aminophenol (Doliprane 100 mg from Sanofi). The mixture was homogenised with a homogenizer mixer at a speed of 400 rpm during 5 minutes.

In a second step (ii), 100 μL of a solution of golf (III) chloride trihydrate (520918-1G from Sigma-Aldrich) (200 mM) was introduced into the mixture at a speed of 400 rpm during 15 minutes.

After the addition of the solution of gold (III) chloride trihydrate by continuous injection, the color of the aqueous gel ink was brown.

When the obtained aqueous gel ink was written on cellulosic paper, the color did not changed and remained brown.

Thus, the color of the ink is the same before application on the cellulosic paper and after application on cellulosic paper.

Comparative Example 2: Preparation of an Aqueous Gel Ink Based on Hydroxylamine and Silver Nanoparticles, without Iron Powder In a first step, a gel-based matrix of aqueous ink was prepared by mixing 180 g of triethylene glycol (solvent), 48 g of polyethylene glycol (solvent), 2.3 g of Acticide® MBS (antimicrobial agent), and 1.20 g of Additie® RC8221 (corrosion inhibitor). The mixture was homogenised with a homogenizer mixer at a speed of 15 m·s$^{-1}$ during 15 minutes and heated at a temperature of 35° C. Then, 5 g of xanthan gum (rheology modifier) was added to the mixture. The mixture was homogenized with a homogenizing mixer at a speed of 15 m·s$^{-1}$ during 15 minutes at a temperature of 35° C. 960 g of deionized water was slowly added to the mixture. The mixture was left to stand for 2 h30. Then, 3.60 g of Moussee® S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.). Then, 1 mL of the obtained gel-based matrix of aqueous ink was mixed with 500 µL of a solution of hydroxylamine hydrochloride (55459 Honeywell Fluka™) (100 mM). The mixture was homogenised with a homogenizer mixer at a speed of 15 m·s$^{-1}$ during 2 minutes.

In a second step, 200 µL of silver nitrate (9370.1 Carl Roth) (200 mM) was introduced into the mixture, and homogenised at a speed of 400 rpm during 5 to 10 minutes. The mixture changed of color from transparent to opaque.

When the obtained aqueous gel ink with variable color was written on cellulosic paper, the color did not change and remained opaque. The colour could not be seen on the paper.

The invention claimed is:

1. A process for preparing in situ an aqueous gel ink with variable color comprising the following steps:
   (i) preparing a gel-based matrix of aqueous ink comprising an N-Acyl-aminophenol, wherein said hydroxyl group is in meta or in para position on the benzenic group,
   (ii) adding a solution of silver salts to the gel-based matrix of aqueous ink prepared in step (i), to obtain an aqueous gel ink with variable color with silver nanoparticles dispersed therein.

2. The process according to claim 1, wherein the N-Acyl-aminophenol is N-acetyl-para-aminophenol.

3. The process according to claim 1, wherein the total concentration of said N-Acyl-aminophenol in the gel-based matrix of aqueous ink of step (i) ranges from 0.10 to 0.30 mol·L$^{-1}$.

4. The process according to claim 1, wherein the concentration of silver salts in the gel-based matrix of aqueous ink of step (ii) ranges from 0.03 to 0.06 mol·L$^{-1}$.

5. An aqueous gel ink with variable color obtained according to the process of claim 1, comprising of said N-Acyl-aminophenol and silver nanoparticles.

6. The aqueous gel ink according to claim 5, wherein the amount of said N-Acyl-aminophenol ranges from 2 to 5% by weight relative to the total weight of the aqueous gel ink.

7. The aqueous gel ink according to claim 5, wherein the silver nanoparticles have an average particle size ranging from 20 to 200 nm.

8. The aqueous gel ink according to claim 5, wherein the silver nanoparticles are silver nanoparticles with the shape of spheres or polyhedral shape.

9. The aqueous gel ink according to claim 5, wherein the amount of silver nanoparticles ranges from 0.5 to 0.8% by weight relative to the total weight of the aqueous gel ink.

10. The aqueous gel ink according to claim 5, wherein the amount of water ranges from 50 to 95% by weight relative to the total weight of the aqueous gel ink.

11. The aqueous gel ink according to claim 5, further comprising a solvent chosen in the group consisting of glycol ethers, in an amount ranging from 5 to 35% by weight relative to the total weight of the aqueous gel ink.

12. The aqueous gel ink according to claim 5, further comprising:
    an antimicrobial agent, in an amount ranging from 0.01 to 0.5% by weight relative to the total weight of the aqueous gel ink; and/or
    a corrosion inhibitor, in an amount ranging from 0.05 to 1% by weight relative to the total weight of the aqueous gel ink; and/or
    an antifoam agent, in an amount ranging from 0.05 to 1% by weight relative to the total weight of the aqueous gel ink.

13. The aqueous gel ink according to claim 5, further comprising a rheology modifier, in an amount ranging from 0.08 to 2% by weight relative to the total weight of the aqueous gel ink.

14. A method of writing with an aqueous gel ink of variable color comprising the step of writing onto an absorbing support with an aqueous gel ink with variable color according to claim 5.

15. A writing instrument comprising:
    an axial barrel containing an aqueous gel ink with variable color according to claim 5, and
    a pen body which delivers the aqueous gel ink stored in the axial barrel,
    wherein the writing instrument is chosen in the group consisting of gel pens, felt pens, correction fluid, and markers.

16. The process according to claim 1, wherein the hydroxyl group is in para position on the benzenic group.

17. The process according to claim 1, wherein the hydroxyl group is in an N-Acyl-aminophenol of formula HO—R1-NH—CO—R2, wherein R1 is a benzene ring and R2 is an alkyl group comprising from 1 to 6 carbon atoms.

18. The process according to claim 17, wherein R2 is an alkyl group comprising from 1 to 3 carbon atoms.

19. The process according to claim 17, wherein the hydroxyl group is in para position.

20. A process for preparing in situ an aqueous gel ink with variable color comprising the following steps:
    (i) preparing a gel-based matrix of aqueous ink comprising an N-Acyl-aminophenol, wherein said hydroxyl group is in para position on the benzenic group, in an N-Acyl-aminophenol of formula HO—R1-NH—CO—R2, wherein R1 is a benzene ring and R2 is an alkyl group comprising from 1 to 3 carbon atoms, (ii) adding a solution of silver salts to the gel-based matrix of aqueous ink prepared in step (i), to obtain an aqueous gel ink with variable color with silver nanoparticles dispersed therein.

\* \* \* \* \*